United States Patent

Miyazaki

Patent Number: 5,686,314
Date of Patent: Nov. 11, 1997

[54] SURFACE PROCESSING METHOD EFFECTED FOR TOTAL-REFLECTION X-RAY FLUORESCENCE ANALYSIS

[75] Inventor: Kunihiro Miyazaki, Tokyo, Japan

[73] Assignee: Kabushiki Kaisha Toshiba, Kawasaki, Japan

[21] Appl. No.: 358,246

[22] Filed: Dec. 19, 1994

[30] Foreign Application Priority Data

Dec. 20, 1993 [JP] Japan .................. 5-319806
Dec. 7, 1994 [JP] Japan .................. 6-303525

[51] Int. Cl.$^6$ .................. G01N 1/00; G01N 21/70; G01N 33/20
[52] U.S. Cl. .................. 436/177; 436/73; 436/80; 436/81; 436/83; 436/84; 436/172; 436/174; 436/175; 378/44; 378/70; 378/79; 378/86; 156/626.1; 134/902
[58] Field of Search .................. 436/73, 80, 81, 436/83, 84, 172, 174, 175, 177; 378/44, 45, 70, 71, 79, 80, 88; 156/626.1; 134/902

[56] References Cited

U.S. PATENT DOCUMENTS

| | | | |
|---|---|---|---|
| 3,925,660 | 12/1975 | Albert | 250/272 |
| 5,148,457 | 9/1992 | Kubota et al. | 378/70 |
| 5,344,779 | 9/1994 | Kaneko et al. | 436/19 |
| 5,422,925 | 6/1995 | Komatsu | 378/45 |
| 5,426,057 | 6/1995 | Tamaoki | 436/146 |

FOREIGN PATENT DOCUMENTS 4-136738  5/1992  Japan .

OTHER PUBLICATIONS

A. Huber et al. *Proc.–Electrochem. Soc.* 1988, 88–20, 109–112.
P. Eichinger *Proc.–Electrochem. Soc.* 1990 90–11, 227–237.
K Nishihagi et al. *Adv. X–Ray Anal.* 1991 34, 81–89.
S. Kojima *Kurin Tekunoroji* 1992, 20–25.
K. Yakushij et al, *X–sen Bunsekinoshinpo* 1993, 24, 87–95.
K. Sugihara et al, *X–sen Bunseki no Shinpo* 1993, 25, 255–268.
R.S. Hockett *Proc.–Inst. Environ. Sci.* 1993, 39, 432–459.
V. Penka et al. *Fresenius Z. Anal. Chem.* 1989, 333, 586–589.
V. Penka et al. *Spectrochim. Acta* 1989, 44B, 483–490.
R.S. Hockett et al. *J. Electrochem. Soc.* 1989, 136, 3481–3486.
C. Neumann et al, *Spectrochim. Acta* 1991, 46B, 1369–1377.
H. Kondo et al. *Jpn. J. Appl. Phys.* 1992, 31, L11–L13.
W. Berneike *Spectrochim. Acta* 1993, 48B, 269–275.
K. Yakushiji et al. *Jpn. J. Appl. Phys.* 1993, 32, 1191–1196.
N. Tsuchiya *Kobutsugaku Zasshi* 1994, 23, 127–133.
Spectroscopy International vol. 2, No. 2, pp. 26–37, 1990 "Total-Reflection X-ray Fluorescence Spectrometry: Principles and Applications" Reinhold Klockenkamper.
Tsuchiya et al. (1990) Nondestructive Evaluation of Trace Metals and Application to Defect Generation. Extended Abstracts of the 22nd conference on Solid State Devices and Materials, Sendai, pp. 1131–1134.

*Primary Examiner*—Arlen Soderquist
*Attorney, Agent, or Firm*—Finnegan, Henderson, Farabow, Garrett & Dunner, L.L.P.

[57] ABSTRACT

A surface processing method effected before the total-reflection X-ray fluorescence analysis is effected is disclosed. The surface processing is to modify all of the contaminants attached at least to the measurement surface of the wafer into particle-shaped residues. For this purpose, the measurement surface of the wafer is first dissolved by hydrofluoric acid to form a large number of droplets on the measurement surface. Next, the thus formed droplets are dried with the position thereof kept unchanged. After the drying, contaminants attached to the measurement surface of the wafer are left as particle-shaped residues. After this, the measurement surface of the wafer is analyzed by the total-reflection X-ray fluorescence analyzing method.

22 Claims, 11 Drawing Sheets

TOTAL-REFLECTION
X-RAY FLUORESCENCE
ANALYSIS $\phi \leq \phi\text{crit}.$

X-RAY FLUORESCENCE
ANALYSIS $\phi > \phi\text{crit}$

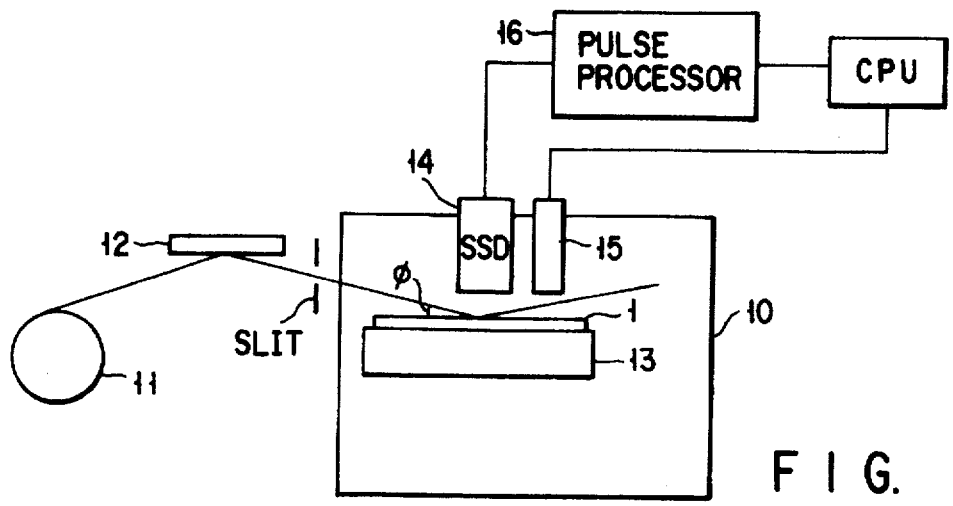
F I G. 7
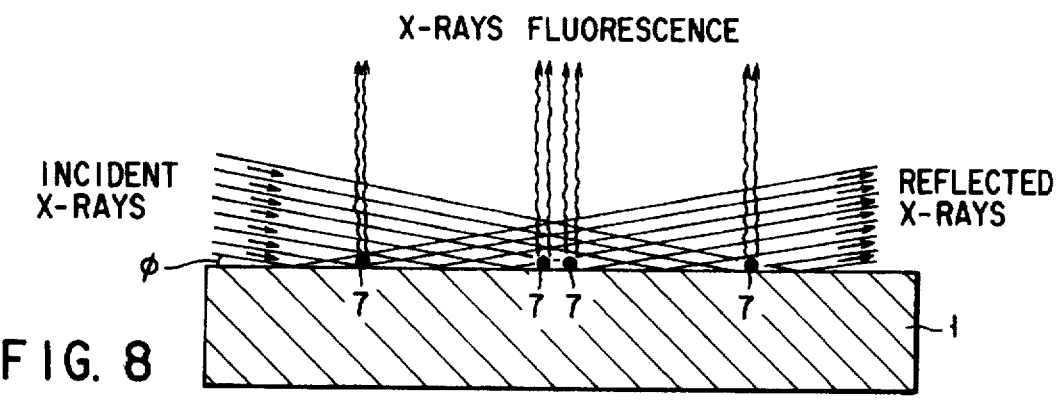
F I G. 8
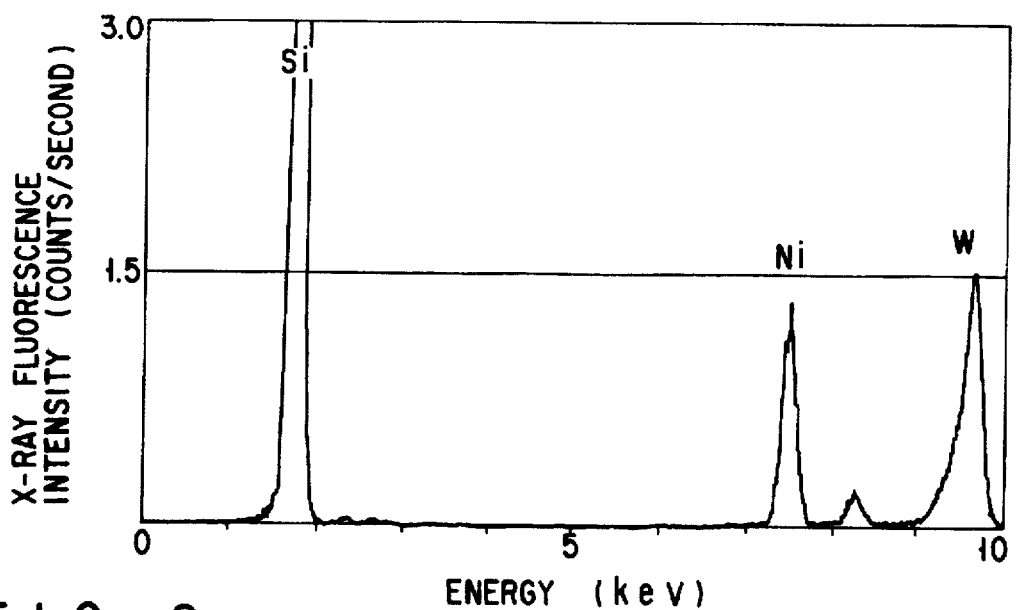
F I G. 9

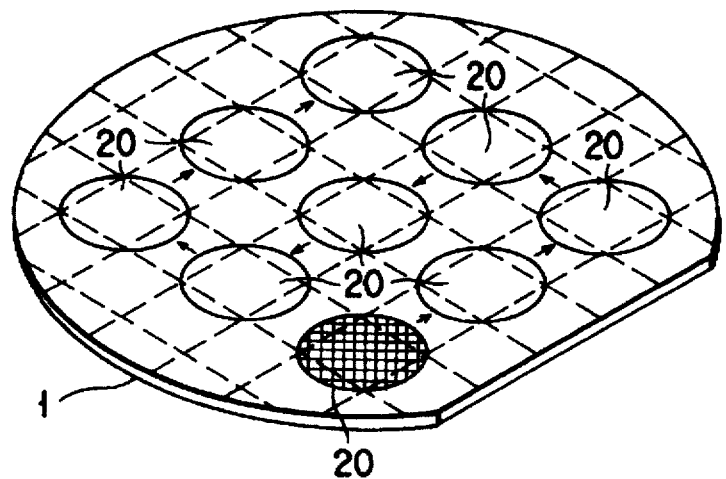
F I G. 10
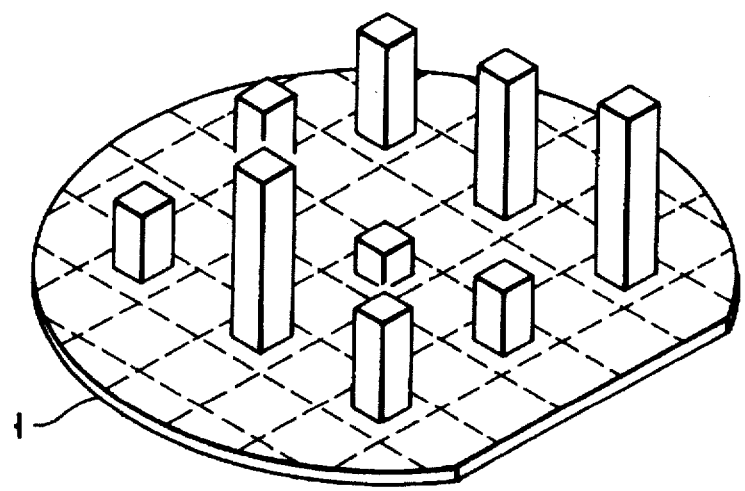
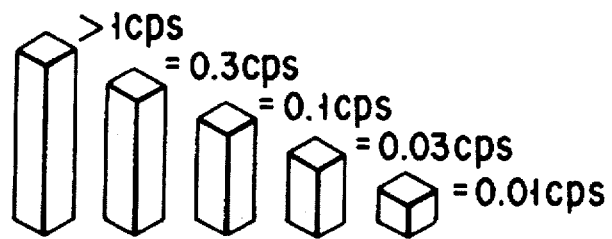
F I G. 11

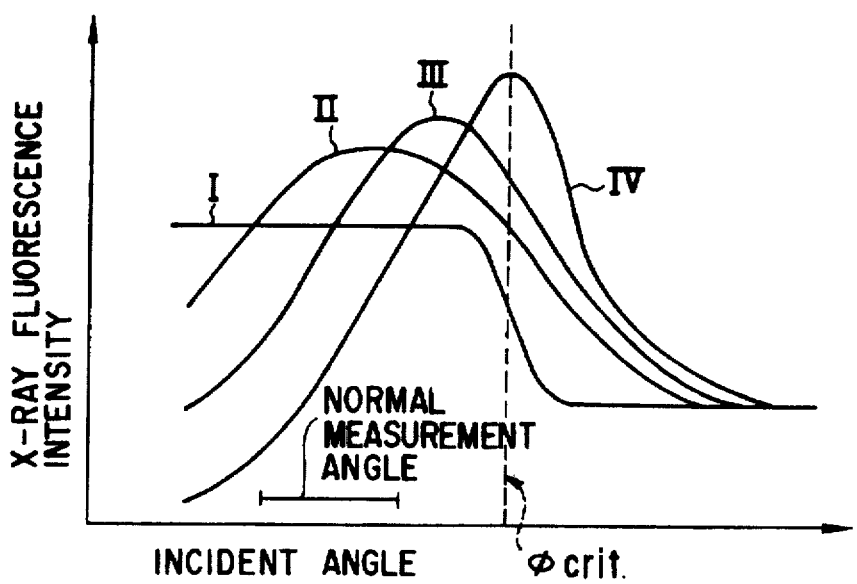
F I G. 19
| | MOISTURE IN CHAMBER | CHARACTERISTIC |
|---|---|---|
| SAMPLE A | 90% OR MORE | I |
| SAMPLE B | 80 % | II |
| SAMPLE C | 70 % | III |
| SAMPLE D (FILM-SHAPED) | — | IV |
F I G. 20

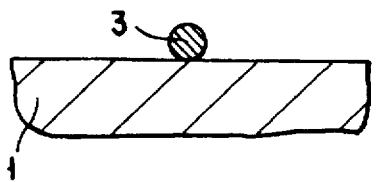
F I G. 21A
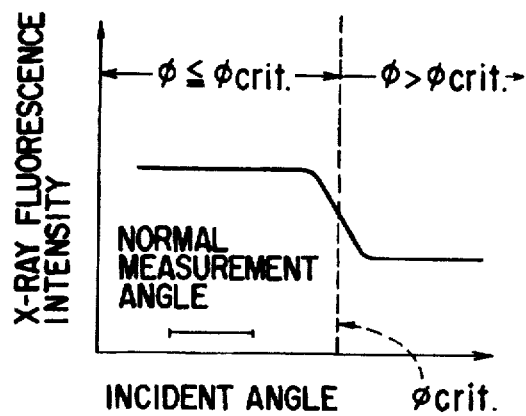
F I G. 21B
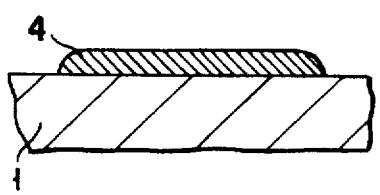
F I G. 22A
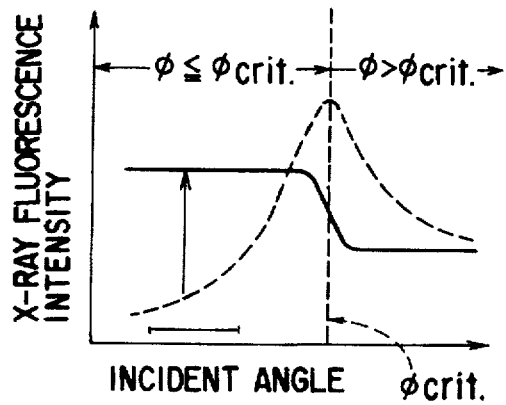
F I G. 22B
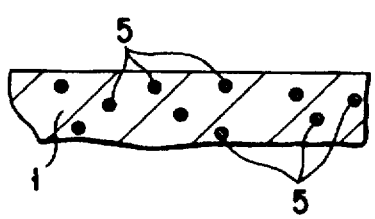
F I G. 23A
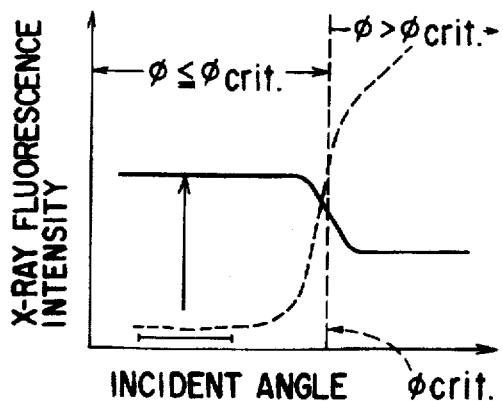
F I G. 23B

5,686,314

SURFACE PROCESSING METHOD EFFECTED FOR TOTAL-REFLECTION X-RAY FLUORESCENCE ANALYSIS

BACKGROUND OF THE INVENTION

1. Field of the Invention

This invention relates to a surface processing method, and more particularly to a surface processing method effected before the total-reflection X-ray fluorescence analysis is effected.

2. Description of the Related Art

The total-reflection X-ray fluorescence analyzing method is gradually put into practice for the contamination management in the semiconductor process. This method enables analysis of a very small amount of impurities (contaminants) which may be present on the surface of a semiconductor wafer or in the surface regions thereof. In addition, the method enables many kinds of elements to be analyzed at one time.

The total-reflection X-ray fluorescence analyzing method utilizes the total-reflection phenomenon that the incident X-ray does not penetrate into a deep portion of the wafer and is reflected on the wafer surface if X-rays are made incident on the wafer surface at an extremely small angle. By utilizing the total reflection phenomenon, the scattering of incident X-rays and a projection of the background due to application of X-ray fluorescence from a base material can be suppressed in comparison with a case of the conventional X-ray fluorescence analyzing method, making it possible to effect the analysis with high sensitivity.

The total-reflection X-ray fluorescence analysis is explained below.

FIG. 1 is a diagram showing the principle of the total-reflection X-ray fluorescence analysis and FIG. 2 is a diagram showing the principle of the ordinary X-ray fluorescence analysis.

As shown in FIG. 1, an incident angle which may cause the total-reflection phenomenon, that is, an angle generally called a total-reflection critical angle ($\phi$crit) is present, and the total-reflection phenomenon occurs when the relation between the incident angle $\phi$ of the X-ray and the total reflection critical angle $\phi$crit is $\phi \leq \phi$crit.

In contrast, if the relation between the incident angle of the X-ray and the total reflection critical angle $\phi$crit is $\phi > \phi$crit as shown in FIG. 2, the X-rays are penetrated into the wafer so that the total reflection phenomenon will not occur.

As shown in FIG. 1, in the total-reflection X-ray fluorescence analysis, since X-ray fluorescence 104 is obtained from contaminants by application of two types of X-rays including incident X-rays 100 and reflected X-rays 102, the intensity of the X-ray fluorescence 104 is substantially doubled in comparison with a case of the ordinary X-ray fluorescence analysis shown in FIG. 2.

Further, in the total-reflection X-ray fluorescence analysis, the amount of X-ray fluorescence from elements constituting the wafer is reduced and scattered X-rays 106 (FIG. 2) caused by the incident X-rays 100 which penetrate into the wafer are not substantially generated. This is because the incident X-rays 100 do not penetrate the interior of the wafer.

Further, the intensity of X-ray fluorescence obtained by the above analyzing methods is proportional to the concentration of contamination elements. That is, if the concentration of contamination elements is high, the intensity of X-ray fluorescence becomes high, and if the concentration is low, the intensity becomes low. Based on the above property of the X-ray fluorescence, the quantitative analysis of contaminant can be made.

However, it is proved that a phenomenon that the intensity (magnitude) of X-ray fluorescence varies not only with the concentration of contaminant elements but also with the shape of the contaminant occurs.

FIGS. 3A, 4A and 5A are cross sectional views schematically showing the shapes of contaminants, and FIGS. 3B, 4B and 5B are diagrams showing the relation between the X-ray incident angle $\phi$ and the intensity of X-ray fluorescence.

In FIG. 3A, the first shape of contaminant is shown. The first shape is a particle shape of contaminant 3 attached on the surface of a wafer 1. The typical example of the particle-shaped contaminant is contaminant attached to the wafer while the wafer is being transferred, for example, and is generally called dust. In FIG. 3B, the relation between the X-ray incident angle $\phi$ and the intensity of X-ray fluorescence when the contaminant takes a particle shape is shown.

In FIG. 4A, the second shape of contaminant is shown. The second shape is a film shape of contaminant 4 spread on the surface of the wafer 1. The typical example of the film-shaped contaminant is contaminant accidentally attached to the wafer surface in the wafer cleaning process and spread on the wafer surface. Such a contaminant is produced, for example when the molecules or ions of the contaminant attach to the surface of the wafer. In FIG. 4B, the relation between the X-ray incident angle $\phi$ and the intensity of X-ray fluorescence when the contaminant takes a film shape is shown. In FIG. 5A, the third shape of contaminant is shown. The third shape is contaminants 5 diffused into the wafer 1. The typical example of the diffused contaminants is contaminants caused by contaminants which are attached to the wafer and diffused into the wafer 1 in the high-temperature heat treatment for the wafer 1, for example. In FIG. 5B, the relation between the X-ray incident angle $\phi$ and the intensity of X-ray fluorescence when the contaminants are diffused into the wafer 1 is shown.

As shown in FIGS. 3B, 4B and 5B, the X-ray fluorescence intensity characteristic varies according to the shape of the contaminant. If the contaminants of the wafer 1 are quantitatively analyzed in the total reflection X-ray fluorescence analyzing method, without the shape of the contaminants checked, the precision of the quantitative analysis is inevitably low, due to the differences in fluorescence X-ray intensity.

In this condition, the limit of detection is said to be approx. $10^{10}$ atoms/cm$^2$ in the total-reflection X-ray fluorescence analysis. However, in recent years, the semiconductor device is increasingly miniaturized and it is required to suppress the evaluation of quantity for the precision of the contaminant analysis in the semiconductor process to $10^{10}$ atoms/cm$^2$ or less.

In order to solve the above problems, a method for collecting contaminants attached to the wafer surface in one place and then effecting the total-reflection X-ray fluorescence analysis is known (Reference Document: Tsuchiya, N., Tanaka, M., Kageyama, M., Kubota, A. and Matsushita, Y., (1990): Nondestructive Evaluation of Trace Metals and Application to Defect Generation. Ext. Abst. 22nd Conf. Solid State Devices and Materials, Sendai, 1131–1134.

However, with this method, information on positions in which the contaminants are attached cannot be obtained. This is because the contaminants attached to the wafer surface are collected into one place.

Information on positions in which the contaminants are attached on the wafer surface, that is, information of in-plane distribution of contaminants can be effectively used for investigation of sources of contamination and cleaning in the semiconductor process.

SUMMARY OF THE INVENTION

A first object of this invention is to provide a surface processing method capable of obtaining at least information of in-plane distribution of contaminant attached to the measurement surface of a to-be-measured subject and making it possible to effect the highly precise quantitative analysis of the concentration of contaminant.

A second object of this invention is to provide a surface processing method capable of obtaining information of in-plane distribution of not only contaminant attached to the measurement surface of a to-be-measured subject but also contaminant penetrating into the subject and making it possible to effect the highly precise quantitative analysis of the concentration of contaminant.

A third object of this invention is to provide a subject surface processing method capable of attaining the first and second objects even if the subject is not hydrophobic.

A fourth object of this invention is to provide a subject surface processing method capable of more stably prevent the in-plane movement of contaminant attached to the measurement surface of a subject or penetrating into the subject in the methods for attaining the first to third objects.

A fifth object of this invention is to provide a subject surface processing method capable of more precisely effect the quantitative analysis of contaminant attached to the measurement surface of a subject or penetrating into the subject in the methods for attaining the first to fourth objects.

In order to attain the first object, in this invention, contaminant which will lie at least on the measurement surface of a subject is dissolved and entrapped into a large number of droplets. After this, the large number of droplets are dried. As a result, the residue of particle-shaped contaminants is obtained. Then, the measurement surface on which the residue is obtained is subjected to the total-reflection X-ray fluorescence analysis.

In order to attain the second object, in this invention, the surface area of the subject is further dissolved.

In order to attain the third object, in this invention, a large number of droplets of solvent are formed on the measurement surface of the subject, contaminant which will lie at least on the measurement surface of the subject is dissolved and entrapped into the large number of droplets. After this, the large number of droplets are dried. As a result, the residue of particle-shaped contaminants is obtained. Then, the measurement surface on which the residue is obtained is subjected to the total-reflection X-ray fluorescence analysis.

In order to attain the fourth object, in this invention, the subject is heated when contaminant which will lie at least on the measurement surface of the subject is dissolved.

In order to attain the fifth object, in this invention, the height of the particle-shaped residue is set to at least 0.1 μm.

With the above subject surface processing method, contaminant is entrapped into a large number of droplets without causing substantial movement in the measurement surface. After this, the large number of droplets are dried, and as a result, the residue of particle-shaped contaminants is obtained. Then, the measurement surface on which the residue is obtained is subjected to the total-reflection X-ray fluorescence analysis and information of in-plane distribution of contaminant attached at least to the measurement surface can be obtained. Further, if the contaminant obtained as the particle-shaped residue is quantitatively analyzed in the total-reflection X-ray fluorescence analyzing method, the most intense X-ray fluorescence is obtained within the range of measurement incidence angles which are narrower than the critical angle. The precision of the quantitative analysis is further enhanced thereby.

By further dissolving the surface area of the subject, contaminant lying on the surface area of the subject can be left as the particle-shaped residue. Therefore, information of in-plane distribution of the contaminant lying on the surface area of the subject can be obtained together with the precise quantitative value of the concentration of the contaminant.

Further, by forming a large number of droplets of solvent on the measurement surface of the subject, contaminant which will lie on the measurement surface of the subject can be entrapped into the large number of droplets even if the subject is not hydrophobic.

Further, by heating the subject when contaminant which will lie at least on the measurement surface of the subject is dissolved, an unwanted liquid can be evaporated. Therefore, condensation or swelling of the liquid for forming the droplets can be prevented, thereby preventing the contaminant from moving to a large extent inside the liquid.

If the height of the particle-shaped residue is set to be 0.1 μm or more, the intensity of the X-ray fluorescence does not vary with a change in the incidence angle, within the range of the measurement incidence angles. Therefore, the precision of the quantitative analysis is further enhanced. Therefore, the quantitative analysis of the contaminant can be more precisely effected.

The upper limit of the height of the particle-shaped residue is determined by the precision of analysis of the total-reflection X-ray fluorescence analyzing device, but in practice, it may be approx. 3 μm.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 7 is a construction diagram of a total-reflection X-ray fluorescence analyzing device;

FIG. 8 is a cross sectional view showing a wafer to which X-rays are irradiated;

FIG. 9 is a diagram showing the result of analysis;

FIG. 10 is a view showing the measurement point on the wafer;

FIG. 11 is a view showing the in-plane distribution of contaminant element and the distribution of concentration;

FIGS. 15A to 18A are cross sectional views respectively showing the droplets growing steps;

FIGS. 15B to 18B are cross sectional views showing particle-shaped residues obtained in each growing step;

FIG. 19 is a diagram showing the relation between the height H of particle-shaped residue and the intensity of X-ray fluorescence;

FIG. 20 is a diagram showing the result of experiments;

FIGS. 21A to 23A are cross sectional views schematically showing the shapes of contaminants;

FIG. 21B is a diagram showing the relation between the X-ray incident angle $\phi$ and the intensity of X-ray fluorescence for the contaminant shown in FIG. 21A;

FIG. 22B is a diagram showing the relation between the X-ray incident angle $\phi$ and the intensity of X-ray fluorescence for the contaminant shown in FIG. 22A; and FIG. 23B is a diagram showing the relation between the X-ray incident angle $\phi$ and the intensity of X-ray fluorescence for the contaminant shown in FIG. 23A.

DETAILED DESCRIPTION OF THE PREFERRED EMBODIMENTS

Figure 1:
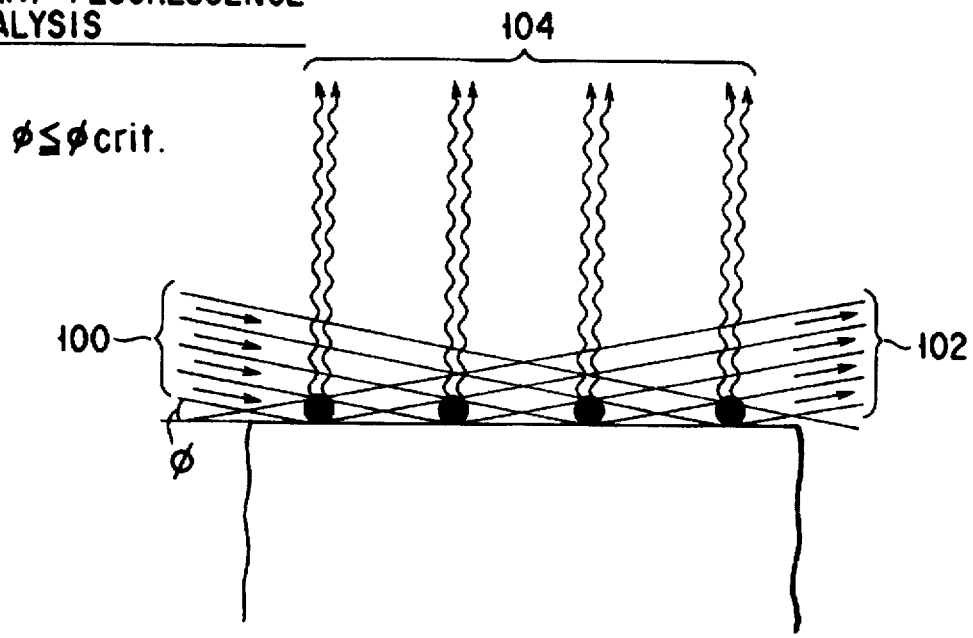
FIG. 1 is a diagram showing the principle of the total-reflection X-ray fluorescence analysis.
Figure 2:
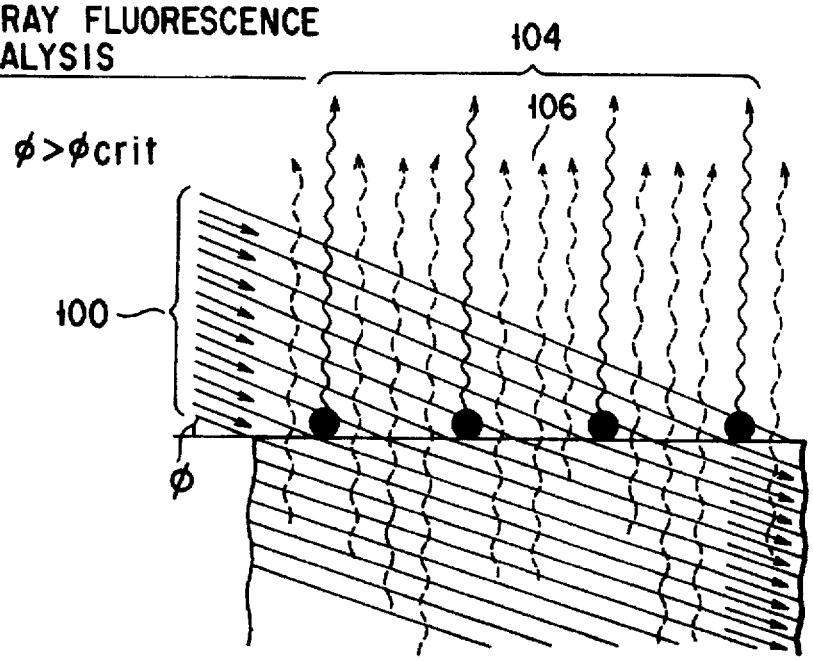
FIG. 2 is a diagram showing the principle of the ordinary x-ray fluorescence analysis.
Figure 3A:
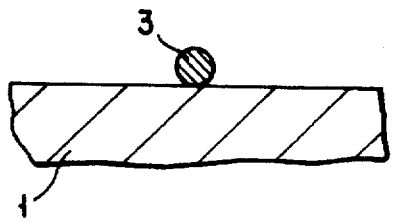
FIGS. 3A, 4A and 5A are cross sectional views schematically showing the shapes of contaminants.
Figure 3B:
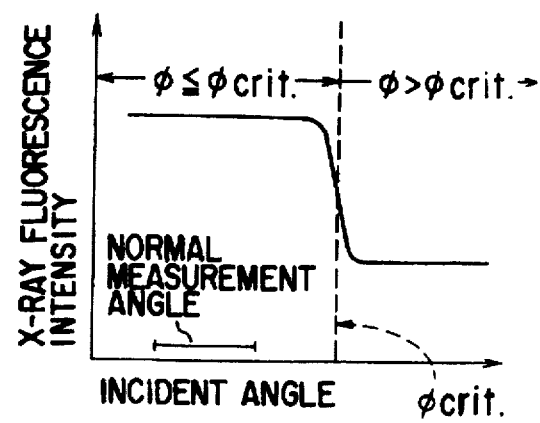
FIG. 3B is a diagram showing the relation between the X-ray incident angle φ and the intensity of X-ray fluorescence for the contaminant shown in FIG. 3A.
Figure 4A:
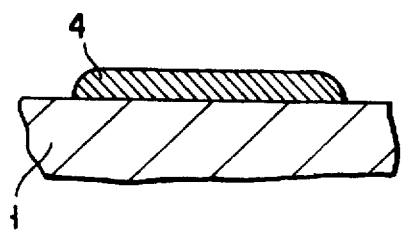
Figure 4B:
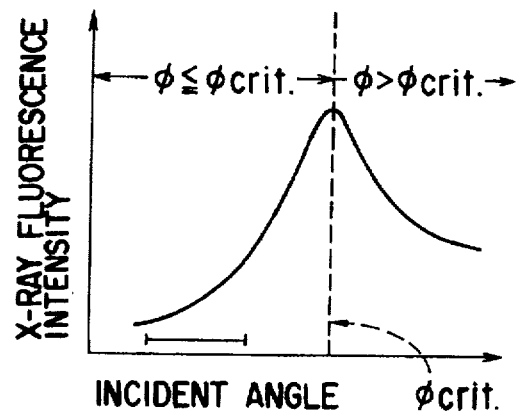
FIG. 4B is a diagram showing the relation between the X-ray incident angle φ and the intensity of X-ray fluorescence for the contaminant shown in FIG. 4A.
Figure 5A:
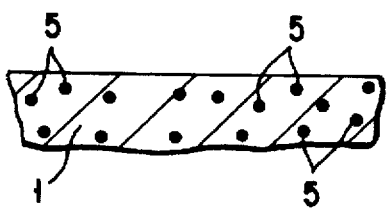
Figure 5B:
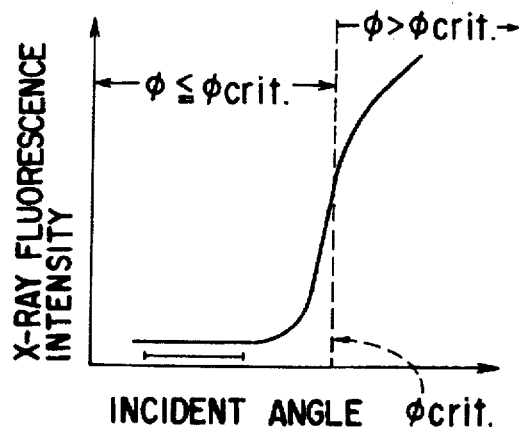
FIG. 5B is a diagram showing the relation between the X-ray incident angle φ and the intensity of X-ray fluorescence for the contaminant shown in FIG. 5A.

There will now be described an embodiment of this invention with reference to the accompanying drawings. In this explanation, portions which are common throughout the drawings are denoted by the same reference numerals and repetitive explanation therefor is omitted.

FIGS. 6A to 6E are cross sectional views showing the main steps of a wafer surface processing method according to a first embodiment of this invention. FIG. 7 is a construction diagram showing the schematic construction of a total-reflection X-ray fluorescence analyzing device. FIG. 8 is a cross sectional view showing a wafer which is subjected to the total-reflection X-ray fluorescence analysis.

Figure 6A:
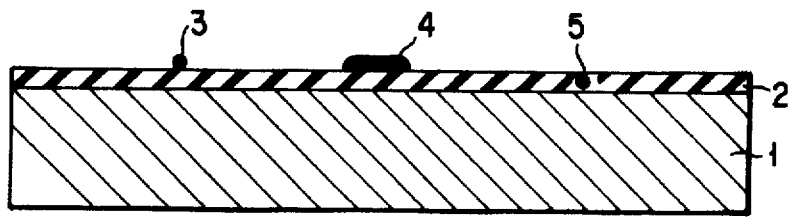
FIGS. 6A to 6E are cross sectional views showing the main steps of a wafer surface processing method according to a first embodiment of this invention.

First, as shown in FIG. 6A, a silicon wafer 1 which is a to-be-measured subject is prepared. A native oxide film ($SiO_2$) 2 which is formed by reaction with oxygen or water in the atmosphere is grown on the surface of the wafer 1. The thickness of the native oxide film 2 is normally approx. 10 to 20 angstrom. Particle-shaped contaminant 3 and film-shaped contaminant 4 lie on the native oxide film 2. Further, diffused contaminant 5 is present in the native oxide film 2.

Figure 6B:
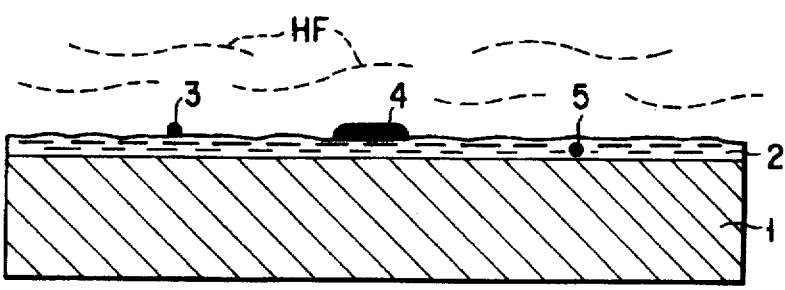
Figure 6C:
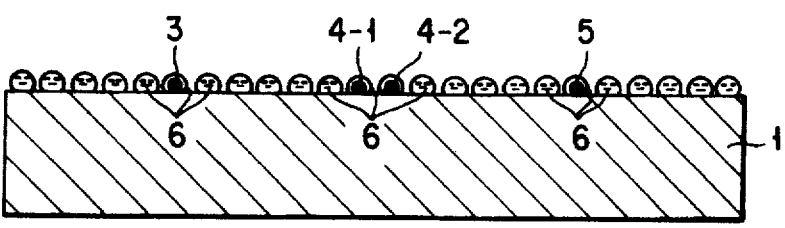

Next, as shown in FIG. 6B, the wafer 1 is fed into a chamber (not shown). Then, hydrofluoric acid vapor (HF) is supplied into the chamber. By the hydrofluoric acid vapor, the surface area portion (native oxide film 2 in this embodiment) of the wafer 1 is dissolved. As a result, the surface area portion is liquefied, for example. Then, dissolution of the native oxide film 2 reaches the surface of the silicon wafer. Silicon has a hydrophobic property. Therefore, as shown in FIG. 6C, a solution obtained by dissolving the native oxide film 2 is formed into a large number of small droplets 6 which are rounded by the surface tension. In this case, 10 the composition of the solution (dropslets) can be considered to be a mixed liquid of $H_2SiF_6$ and $H_2O$. The estimated chemical reaction formula is as follows. 6HF (hydrofluoric acid)+$SiO_2$ (native oxide film)→$H_2SiF_6$ and $2H_2O$ By forming the large number of droplets 6, the particle-shaped contaminant 3, film-shaped contaminant 4 and diffused contaminant 5 are dissolved into the droplets 6.

At this time, the particle-shaped contaminant 3 lying on the native oxide film 2 is entrapped into the droplets 6 only by the substantial vertical movement without causing the substantial plane movement.

Further, the film-shaped contaminant 4 lying on the native oxide film 2 is dissolved by hydrofluoric acid. After this, the contaminant is dispersedly dissolved into a plurality of droplets 6 only by the substantial vertical movement without causing the substantial plane movement in the same manner as described above (refer to reference numerals 4-1, 4-2). When the film-shaped contaminant 4 is dispersedly dissolved into the plurality of droplets 6, the shape thereof is changed into a shape similar to that of the particle-shaped contaminant 3.

Further, the diffused contaminant 5 is dissolved into the droplets 6 only by the substantial vertical movement without causing the substantial plane movement in the same manner as described above.

When the contaminants 3, 4 and 5 are dissolved into the droplets 6, they slightly move on the surface of the wafer 1. However, the slight vertical movement which may be caused by contaminants 3, 4 and 5 would not adversely affect the precision of analysis since the X-ray fluorescence detector is located just above the wafer 1 when the total-reflection X-ray fluorescence analysis is performed.

Figure 6D:
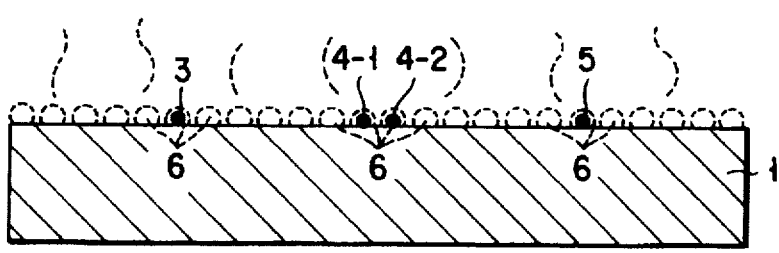
Figure 6E:
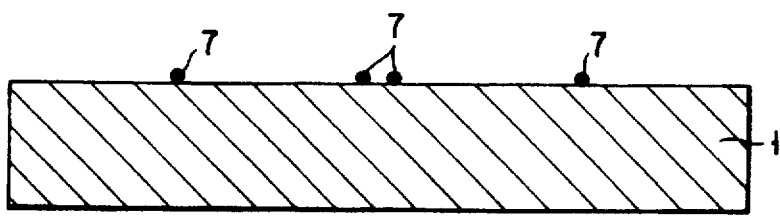

Next, as shown in FIG. 6D, the wafer 1 is dried without moving the droplets 6 formed on the measurement surface of the wafer 1 to remove the mixed liquid of $H_2SiF_6$ and $H_2O$. After drying, only the salts of the contaminants are left on the silicon ground, that is, the measurement surface of the wafer 1 as shown in FIG. 6E. Therefore, the particle-shaped residues 7 formed of contaminants are obtained. At this time, all of the contaminants are modified into particle-shaped residues irrespective of whether the original contaminants are particle-shaped contaminants, film-shaped contaminants or diffused type contaminants.

Next, the wafer 1 on the surface of which the particle-shaped residues 7 are obtained is fed into a sample chamber 10 of the total-reflection X-ray fluorescence analyzing device of FIG. 7. As the analyzing device, a device which is known in the art is used.

The known device includes a rotary cathode 11 for generating X-rays with tungsten, molybdenum and gold, for example, used as a source, and a monochromator 12 for extracting an X-ray of specified wavelength from the X-rays generated from the rotary cathode 11. The X-ray of specified wavelength is guided into the processing chamber 10 and made incident on the surface of the wafer 1 placed on a sample table 13. As shown in FIG. 8, the X-ray is incident on the surface of the wafer 1 in a condition of the incident angle $\phi \leq$ the total reflection critical angle $\phi$crit. Therefore, the total reflection phenomenon occurs.

The sample table 13 is a stage which can be moved in a plane direction and permits precise setting of the incident angle. A solid state detector (SSD) 14 for detecting X-ray fluorescence generated from the particle-shaped residues 7 and a displacement sensor 15 for detecting the amount of movement of the sample table 13 are mounted above the sample table 13. The solid state detector 14 is connected to a pulse processor 16.

The pulse processor 16 derives the spectrum of detected X-ray fluorescence. An example of the analyzing result by the pulse processor 16 is shown in FIG. 9.

As shown in FIG. 9, in the X-ray fluorescence analysis, the energy peak characteristic to each element is obtained. For example, the first peak of X-ray fluorescence intensity can be observed in the range of 1.5 to 2.0 keV, the second peak can be observed in the range of 7.2 to 7.7 keV, and the third peak can be observed in the range of 9.0 to 10.0 keV. Based on the peaks, the types of elements can be determined (Reference Document: Reinhold Klockenkamper, "Total-Reflection X-ray Fluorescence Spectrometry: Principles and Applications" Spectroscopy International 2(2), 1990, p26 to p37.).

In the result of analysis shown in FIG. 9, the first peak is caused by silicon (Si) constituting the wafer 1 and the third peak is caused by tungsten (W) used as a source of X-rays. Further, it is understood that the second peak is caused by nickel (Ni) from the energy peak position of 7.47 keV. That is, nickel is present as the impurity in the surface portion of the wafer 1.

Further, although not detected in the result of analysis shown in FIG. 9, iron (Fe), zinc (Zn), chromium (Cr), potassium (K) and calcium (Ca) are present as measurable elements in addition to nickel. The elements are contaminants which may cause contamination in the semiconductor process.

The above measurement is effected for the entire surface of the wafer 1 as shown in FIG. 10 while the sample table 13 is being moved. A plurality of areas indicated by a reference numeral 20 in FIG. 10 are the measurement points. The measurement result shown in FIG. 9 is obtained for each of the measurement points 20. When the measurement results for all of the measurement points 20 are obtained, the intensity of X-ray fluorescence at the energy peak obtained for each contaminant element is plotted for each measurement point 20. Next, the measurement result is processed by a computer. In this process, it may be preferable to form a 3-dimensional column-like image whose height represents the concentration of contaminant element on each measurement point as shown in FIG. 11, for example. By forming such an image, the operator can understand the distribution of concentration and the in-plane distribution of contaminant elements at a glance. The broken lines indicated on the wafer 1 in FIGS. 10 and 11 represent the coordinates.

Next, the surface processing method according to a second embodiment of this invention is explained.

FIGS. 12A to 12F are cross sectional views showing the main steps of the wafer surface processing method according to the second embodiment of this invention.

The first embodiment is an example in which only the native oxide film 2 on the surface of the wafer 1 is dissolved, but the second embodiment is an example in which a bulk portion of the wafer 1 is also dissolved. By this, the in-plane distribution of contaminant lying in the bulk portion can be detected. Further, the second embodiment contains a method for adjusting the amount of dissolved portion of the wafer 1.

Figure 12A:
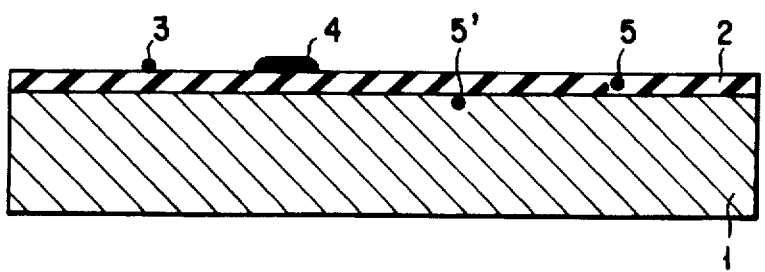
FIGS. 12A to 12F are cross sectional views showing the main steps of a wafer surface processing method according to a second embodiment of this invention.

First, as shown in FIG. 12A, particle-shaped contaminant 3 and film-shaped contaminant 4 lie on the native oxide film 2 and diffused contaminant 5 lies inside the native oxide film 2 like the case of the sample explained with reference to FIG. 6A. Further, in the sample shown in FIG. 12A, diffused contaminant 5' lies inside a bulk portion of the wafer 1 which is near the silicon ground surface.

Figure 12B:
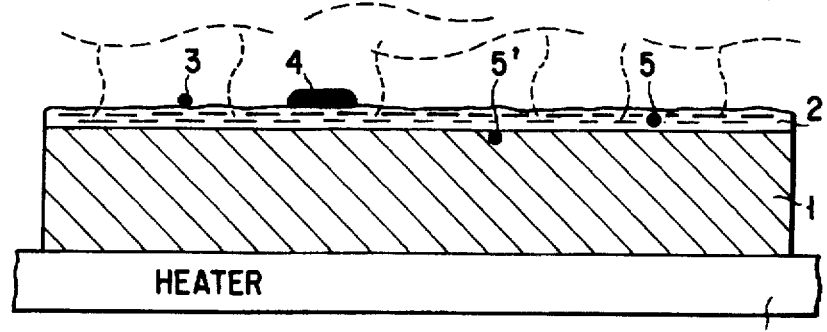
Figure 12C:
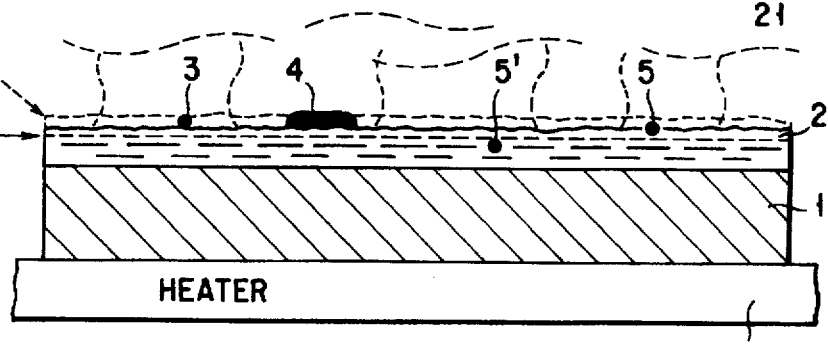

Next, as shown in FIG. 12B, the wafer 1 is fed into a chamber (not shown). Then, in order to form droplets on the surface of the wafer 1 in the chamber, the surface area portion of the wafer 1 or the native oxide film 2 in this embodiment and the neighboring portion of the silicon surface are dissolved by use of hydrofluoric acid +nitric acid vapor (HF+HNO$_3$). Further, in the second embodiment, the above dissolution is effected while the wafer 1 is heated by use of a heater 21, for example. If the dissolution progresses while heating the wafer 1, part of the liquefied native oxide film (SiO$_2$) 2 and part of the liquefied wafer (Si) 1 are evaporated as shown in FIGS. 12B and 12C and the liquefied amount can always be adequately adjusted. By the adjustment, condensation of the droplets due to an increase in the amount of solution or swelling thereof can be prevented, thereby preventing the contaminants 3 to 5' from moving to a large extent in the plane.

Figure 12D:
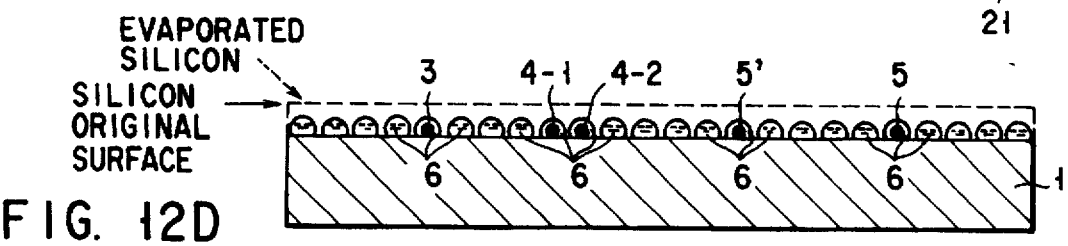

A stage at which dissolution of the bulk portion progresses to some extent is shown in FIG. 12D. In FIG. 12D, the original surface of the silicon surface is indicated by broken lines. Even when the bulk portion is liquefied, a portion which is finally exposed is silicon. Silicon is hydrophobic. Therefore, like the first embodiment, a large number of rounded and small droplets 6 are formed on the surface of the wafer 1.

By formation of the large number of droplets 6, particle-shaped contaminant 3, film-shaped contaminant 4 and diffused contaminants 5 and 5' are entrapped into the droplets 6. At this time, the contaminant 5' diffused into the bulk portion is entrapped into the droplets 6 only by the vertical movement without causing the substantial plane movement like the other contaminants.

Figure 12E:
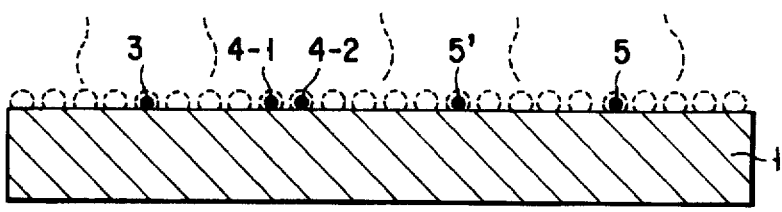
Figure 12F:
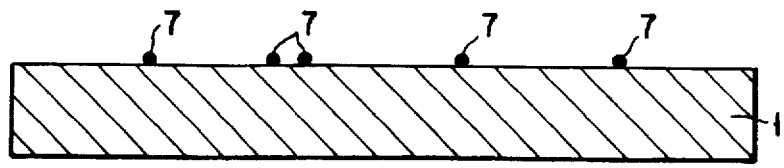

Then, the droplets 6 are dried as shown in FIG. 12E by the same method as that explained with reference to FIGS. 6D and 6E and particle-shaped residues 7 formed of impurities are obtained on the surface of the wafer 1 as shown in FIG. 12F.

After this, like the first embodiment, the surface of the wafer 1 is analyzed by use of the analyzing device shown in FIG. 7 using the total-reflection X-ray fluorescence analyzing method as shown in FIG. 8.

Next, the surface processing method according to a third embodiment of this invention is explained.

FIGS. 13A to 13E are cross sectional views showing the main steps of the wafer surface processing method according to the third embodiment of this invention.

The first and second embodiments are examples in which the surface area portion of the wafer 1 is dissolved, a large number of droplets 6 are formed on the measurement surface of the wafer 1, and contaminants 3, 4 lying on the surface of the wafer 1 and diffused contaminants 5, 5' are entrapped into the droplets 6.

The third embodiment is an example in which a large number of drops of solvent, for example, are formed on the measurement surface of the wafer 1 and contaminants are entrapped into the droplets.

Figure 13A:
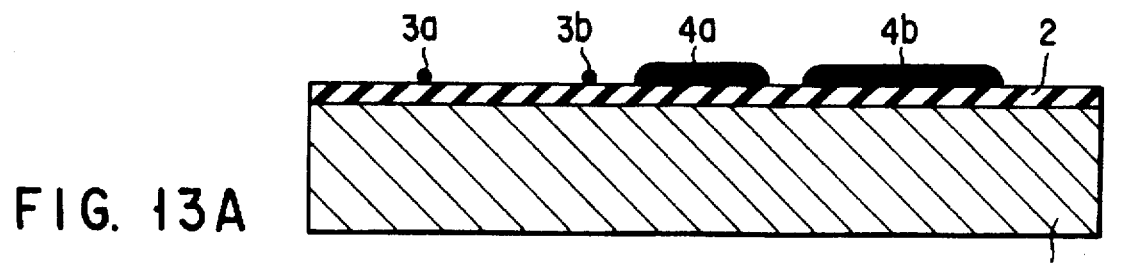
FIGS. 13A to 13E are cross sectional views showing the main steps of a wafer surface processing method according to a third embodiment of this invention.

First, as shown in FIG. 13A, particle-shaped contaminants 3a, 3b and film-shaped contaminants 4a, 4b lie on the native oxide film 2.

Figure 13B:
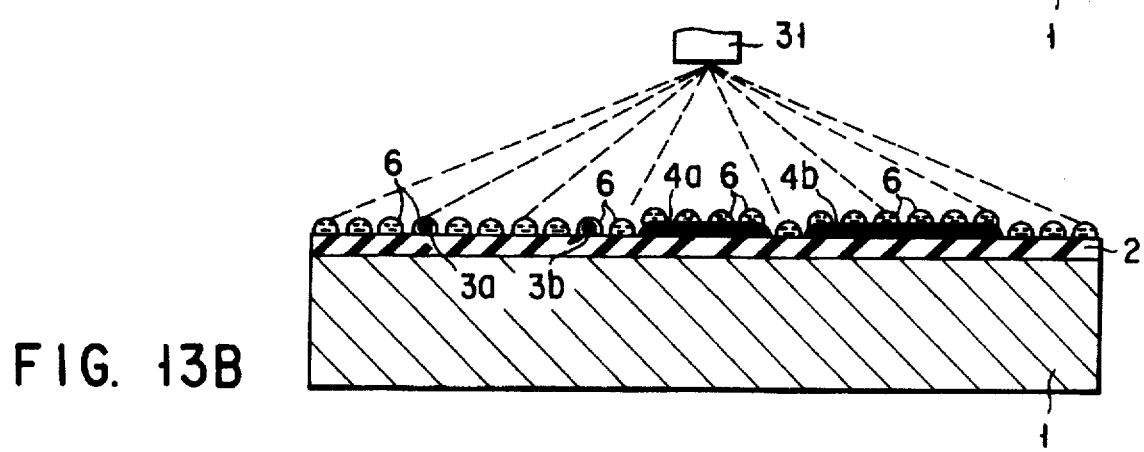
Figure 13C:
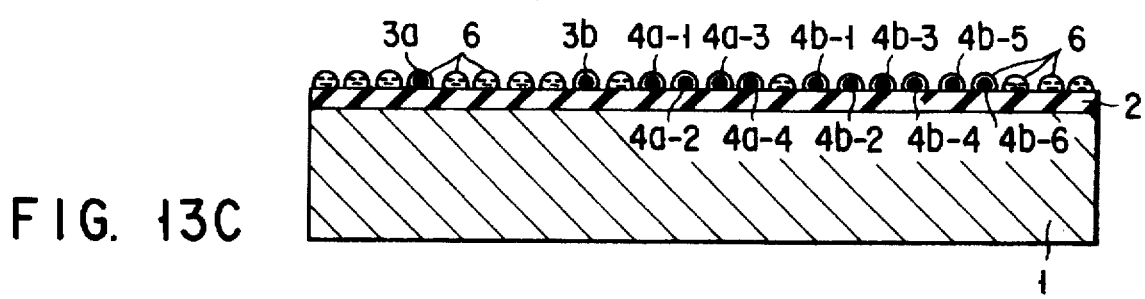
Figure 13D:
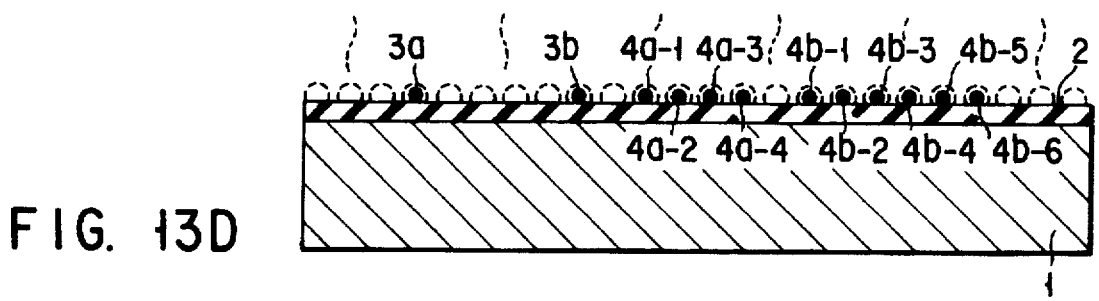

Next, as shown in FIG. 13B, the wafer 1 is fed into a chamber (not shown). Then, a liquid into which the contaminants 3a, 3b, 4a, 4b can be dissolved is sprayed from a nozzle 31 onto the surface of the wafer 1 (onto the native oxide film 2 in this embodiment) in the chamber. By this spraying, a large number of small droplets 6 are obtained on the native oxide film 2 and film-shaped contaminants 4a, 4b. As a spraying means for forming such droplets 6, an ultrasonic nebulize method is used, for example. By this method, a solution of adjusted component can be sprayed and the small droplets 6 formed of the solution can be obtained. The contaminants 3a, 3b, 4a, 4b are dissolved into the large number of droplets 6 with the elapse of time. Then, as shown in FIG. 13C, the contaminants 3a, 3b, 4a, 4b are entrapped into the large number of droplets 6. Particularly, the film-shaped contaminants 4a, 4b are dispersedly entrapped into the droplets 6.

Figure 13E:
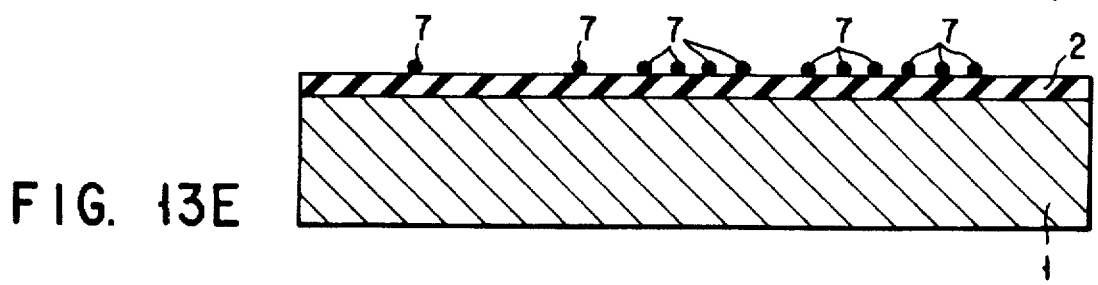

Then, the droplets 6 are dried as shown in FIG. 13E by the same method as that explained with reference to FIGS. 6D to 6F and particle-shaped residues 7 formed of impurities are obtained on the surface of the native oxide film 2 as shown in FIG. 13E.

After this, like the first embodiment, the surface of the wafer 1 is analyzed by use of the analyzing device shown in FIG. 7 using the total-reflection X-ray fluorescence analyzing method as shown in FIG. 8.

Next, the surface processing method according to a fourth embodiment of this invention is explained.

FIGS. 14A to 14E are cross sectional views showing the main steps of the wafer surface processing method according to the fourth embodiment of this invention.

The fourth embodiment is an example which is basically similar to the third embodiment and in which a method for forming droplets on the surface of the wafer 1 is attained by another means and method.

Figure 14A:
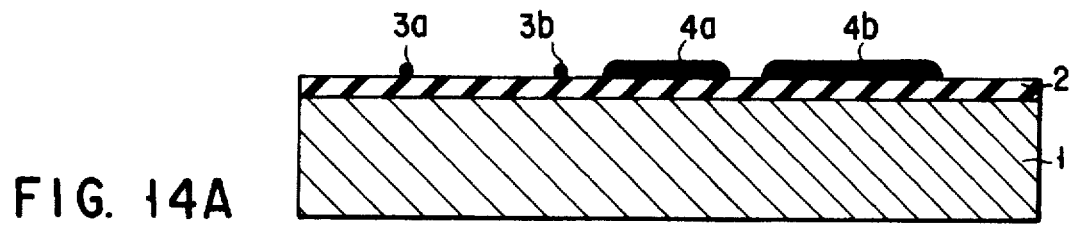
FIGS. 14A to 14E are cross sectional views showing the main steps of a wafer surface processing method according to a fourth embodiment of this invention.

First, as shown in FIG. 14A, particle-shaped contaminants 3a, 3b and film-shaped contaminants 4a, 4b lie on the native oxide film 2.

Figure 14B:
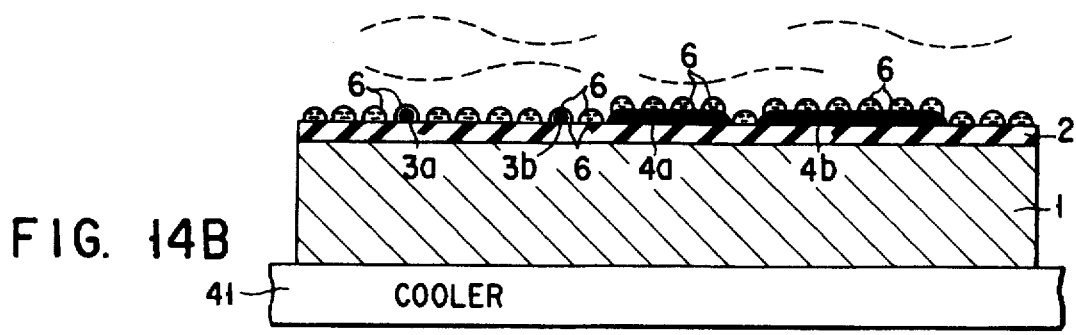
Figure 14C:
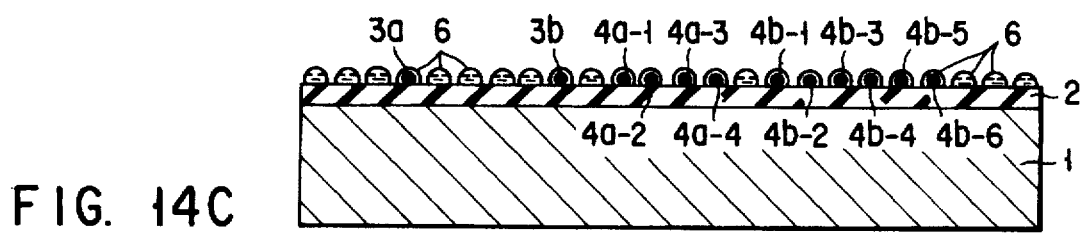

Next, as shown in FIG. 14B, the wafer 1 is fed into a chamber (not shown). Then, a gas of solvent into which the contaminants 3a, 3b, 4a, 4b can be dissolved is supplied into the chamber. Further, the wafer 1 is cooled by a cooler 41, for example. By this cooling process, the solution gas is condensed to make dews on the native oxide film 2 and the film-shaped contaminants 4a, 4b. By the dew condensation, a large number of small droplets 6 are formed on the surface of the wafer 1. Like the third embodiment, the contaminants 3a, 3b, 4a, 4b are subjected to the chemical reaction such as liquefaction by the solution constituting the large number of droplets 6. Then, the contaminants 3a, 3b, 4a, 4b are dissolved with the elapse of time and entrapped into the large number of droplets 6 as shown in FIG. 14C. Particularly, the film-shaped contaminants 4a, 4b are dispersedly entrapped into the droplets 6.

Figure 14D:
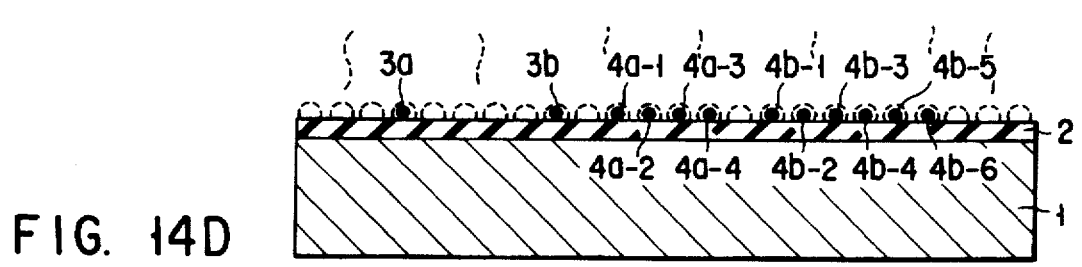
Figure 14E:
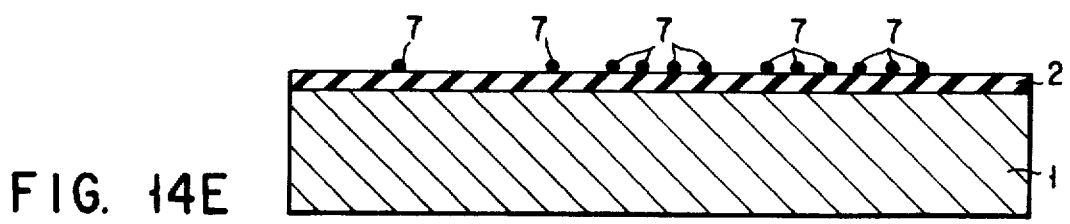

Then, the droplets 6 are dried as shown in FIG. 14D by the same method as that explained with reference to FIGS. 6D to 6F and particle-shaped residues 7 formed of impurities are obtained on the surface of the native oxide film 2 as shown in FIG. 14E.

After this, like the first embodiment, the surface of the wafer 1 is analyzed by use of the analyzing device shown in FIG. 7 using the total-reflection X-ray fluorescence analyzing method as shown in FIG. 8.

In the third and fourth embodiments, the droplets 6 formed of solution are formed on the surface of the wafer 1. In these methods, the surface area portion of the wafer 1 is not liquefied so that information on the in-plane distribution of the contaminant can be obtained without destroying the native oxide film 2 and wafer 1, for example. Further, in these methods, since a large number of droplets 6 formed of solution are formed on the surface of the wafer 1, it becomes possible to effect the surface processing method according to this invention even if the wafer 1 is formed of a material which is not hydrophobic. Of course, the third and fourth embodiments can be applied when the wafer 1 is hydrophobic. Further, as explained in the first and second embodiments, the surface portion of the native oxide film 2 and wafer 1 can be dissolved. Further, as explained in the second embodiment, the process can be effected while heating the wafer 1.

Further, in the third embodiment, since a solution of adjusted components can be sprayed by use of the ultrasonic nebulize method, it is possible to change the solutions, for example, first spray a solution into which impurities can be dissolved, spray a solution into which the native oxide film can be dissolved, and then spray a solution into which silicon can be dissolved, and adjust the amounts of the solutions in a simple manner. From this point of view, it is possible to effect the surface processing while controlling the etching rate of a film formed on the wafer 1.

Further, we reduced the diameters of droplets 6 formed in order to more precisely check the in-plane distribution of contaminants. This attempt was made to attain more precise distribution density of particle-shaped residues 7 by reducing the diameters of the particle-shaped residues 7 formed by drying the droplets 6.

FIGS. 15A to 18A are cross sectional views respectively showing the growing steps of the droplets. Further, FIGS. 15B to 18B are cross sectional views showing the particle-shaped residues obtained in each growing step;

In order to control the diameter of the droplets 6, the amount of material which can be liquefied may be controlled at the reaction temperature at which the chemical reaction occurs, for example, at normal temperatures.

Figure 15A:
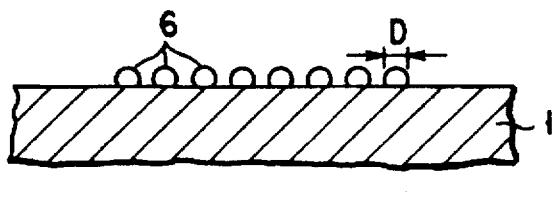
Figure 16A:
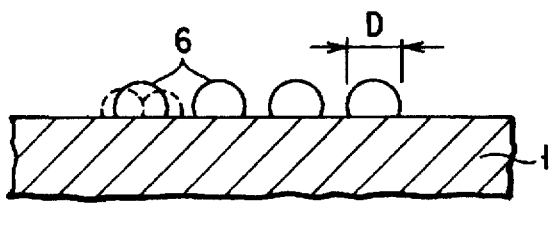
Figure 17A:
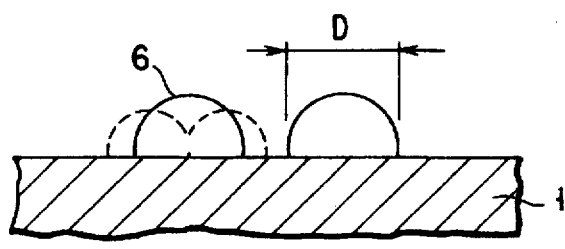

In the chemical reaction formula explained in the first embodiment, the amount of hydrofluoric acid vapor (HF) or water vapor ($H_2O$) may be controlled. In the chemical reaction formula explained in the first embodiment, only the minimum amounts of hydrofluoric acid vapor (HF) and water vapor ($H_2O$) necessary for the chemical reaction are shown, and in this case, the diameter of the droplets 6 is set to the smallest value. This state is shown in FIG. 15A. As the amount of hydrofluoric acid vapor (HF) or Water vapor ($H_2O$) is increased, the diameter of the droplets 6 increases. As the diameter of the droplets 6 increases, adjacent droplets 6 are brought into contact with each other to make a droplets 6. For example, this is shown in FIG. 16A. When this action is repeated, the droplets 6 gradually becomes larger as shown in FIG. 17A and in FIG. 18A.

However, it is confirmed that the precision of the quantitative analysis starts to be lowered when the diameter of the droplets 6 is reduced and the distribution density of the particle-shaped residues 7 is made more precise. The cause of this phenomenon is that the height of the particle-shaped residue 7 is too small.

Figure 15B:
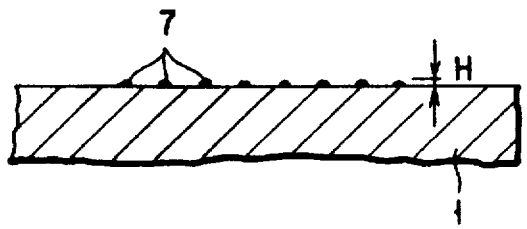
Figure 16B:
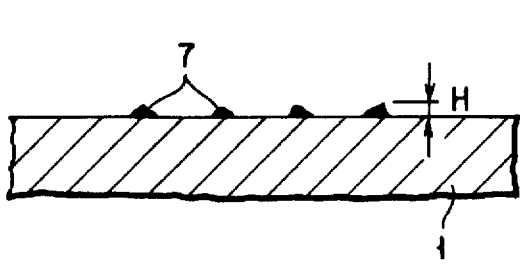
Figure 17B:
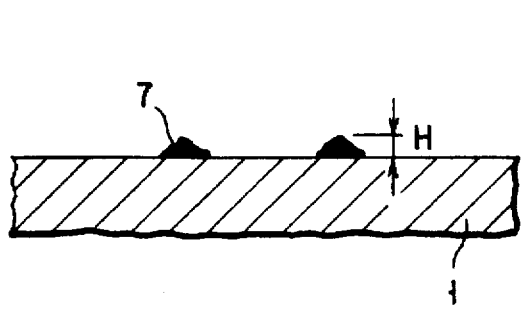
Figure 18A:
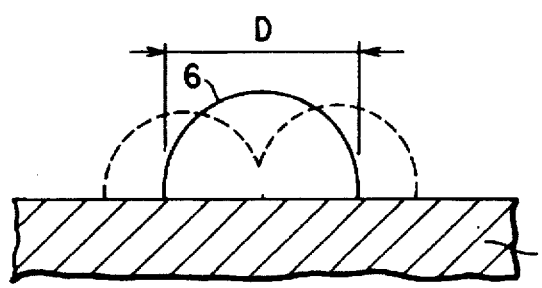
Figure 18B:
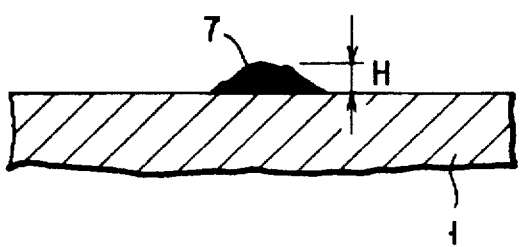

First, if the diameter D of the droplets 6 is small as shown in FIG. 15A, the height H of the particle-shaped residue 7 left after the drying process becomes small as shown in FIG. 15B. As the diameter D of the droplets 6 is gradually increased as shown in FIGS. 16A, 17A and 18A, the height H of the particle-shaped residue 7 left after the drying process becomes larger as shown in FIGS. 16B, 17B and 18B. If the height H of the particle-shaped residue 7 is kept large, the precision of the quantitative analysis is not lowered. However, if the diameter D of the droplets 6 is excessively increased as shown in FIG. 18A, for example, the measurement precision of the in-plane distribution is lowered.

In order to solve the above trade off, an attempt is made to obtain the minimum permissible height of the particle-shaped residue 7 which realizes sufficiently precise quantitative analysis.

FIG. 19 is a diagram showing the X-ray fluorescence intensity characteristic for each height H of the particle-shaped residue 7.

In our experiments, as the processing flow, the surface processing method shown in FIGS. 12A to 12F was used. As the method for adjusting the height of the residue 7, a method for changing the moisture inside the chamber was used. As the method for changing the moisture inside the chamber, a method for changing the moisture in the gas of hydrofluoric acid vapor (HF) supplied into the chamber was used. In order to change the moisture in the gas, the amount of water vapor ($H_2O$) contained in the hydrofluoric acid vapor was changed. The results of the experiments are shown in FIG. 20.

The characteristic indicated by a curve IV in FIG. 19 is obtained in a case film-shaped residue 7. Likewise, the characteristic indicated by a curve III is obtained in a case wherein the height H is set at approx. 0.03 μm, the characteristic indicated by a curve II is obtained in a case wherein the height H is set at approx. 0.05 μm, and the characteristic indicated by a curve I is obtained in a case wherein the height H is set at approx. 0.1 μm.

It is understood from the above results that the characteristic becomes equal to the X-ray fluorescence intensity characteristic of the particle-shaped contaminant if the height H of the particle-shaped residue 7 is set to 0.1 μm or more. That is, if the height H of the particle-shaped residue 7 is set to 0.1 μm or more, the sufficiently high measurement precision of quantitative values can be attained.

Further, in order to prevent the measurement precision of the in-plane distribution from being lowered, the height H of the particle-shaped residue 7 is prevented from being set to an excessively large value. However, the excessively large value of the height H cannot be unconditionally determined. This is because the measurement precision of the in-plane distribution varies according to the analysis precision of the total-reflection X-ray fluorescence analyzing device. However, in order to satisfy the minimum analysis precision which will be required, it will be preferable to set the height H of the particle-shaped residue 7 to 3 μm or less.

In the surface processing method according to this invention as described in the first to fourth embodiments, the surface area portion of the wafer 1 is formed into a large number of droplets 6 by use of a solution gas or solution, or a large number of droplets 6 formed of a solution are formed on the surface thereof. Thus, contaminant to be measured lying on the surface area portion of the wafer 1 can be entrapped into the droplets 6. Then, particle-shaped residues 7 formed of contaminant can be obtained on the surface of the wafer 1 by drying the droplets 6.

With the above surface processing method, the contaminant can be uniformly modified into a particle form as shown in FIG. 21A even if the contaminant lying on the surface portion of the wafer 1 is the film-shaped contaminant as shown in FIG. 22A or diffused type contaminant as shown in FIG. 23A. As a result, when the analyzing process is effected by use of the total-reflection X-ray fluorescence analyzing device, the X-ray fluorescence intensity characteristic can be uniformed as shown in FIGS. 21B, 22B and 23B. Further, as respectively shown in FIGS. 22B and 23B, the X-ray fluorescence intensity characteristic of the film-shaped contaminant and the X-ray fluorescence intensity characteristic of the diffused contaminant can be modified into the X-ray fluorescence intensity characteristic obtained by the particle-shaped contaminant shown in FIG. 21B. Since the strongest X-ray fluorescence can be obtained from the particle-shaped contaminant, the sensitivity of analysis becomes higher. From this point of view, the precision of the quantitative analysis of contaminant elements is enhanced.

Further, at the time of uniforming the shape of the contaminant, it is only necessary to entrap the contaminants into the large number of small droplets 6 and the contaminant will not substantially move in a plane. Therefore, information of the in-plane distribution of contaminant is not lost. As a result, information on the distribution state of contaminant on the wafer surface can be obtained with high precision together with the quantitative value thereof.

As explained in the second embodiment, when the surface portion of the wafer 1 is dissolved while heating the wafer 1, an increase in the amount of solution can be suppressed so as to prevent condensation or swelling of the solution. The method is effective for the analysis which is effected by dissolving a portion to the silicon portion of the wafer 1 and in which the amount of the solution tends to increase, and for the analysis effected by dissolving a thick film when a thermal oxidation film is grown after removing the native oxide film or when a deposition film is additionally formed in the first embodiment.

Further, as explained in the third and fourth embodiments, when the droplets 6 of solution are formed on the surface of the wafer 1, for example, the surface processing method according to this invention can be realized by analyzing the wafer without etching the wafer 1 or the film formed on the wafer 1 or even when the wafer 1 or the film formed on the wafer 1 is not hydrophobic.

In the first to fourth embodiments, the surface processing for the wafer 1 having the native oxide film 2 formed on the surface thereof is explained, but the surface processing method of this invention can be applied to a wafer having a film such as a silicon nitride film ($Si_3N_4$) other than the silicon oxide film ($SiO_2$). When such a wafer is subjected to the surface processing, a solution gas or solution into which the film formed on the surface can be dissolved is selectively used.

As a solution gas or solution into which $SiO_2$ or $Si_3N_4$ can be dissolved, hydrofluoric acid (HF), nitric acid ($HNO_3$), hydrochloric acid (HCl), sulfuric acid ($H_2SO_4$), hydrogen peroxide ($H_2O_2$), ozone ($O_3$) or a mixture of the above materials adequately mixed can be used.

As a gas or solution into which only the contaminant on the surface of the wafer 1 can be dissolved, hydrochloric acid (HCl), nitric acid ($HNO_3$), sulfuric acid ($H_2SO_4$), or a mixture of the above materials adequately mixed can be used.

In the first to fourth embodiments, a silicon wafer for use in a silicon integrated circuit is referred to as a specific example of a subject which is measured and analyzed. However, the processing method of the present invention is applicable not only to such a silicon wafer but also to a GaAs wafer, InP wafer, etc. for use in a compound semiconductor integrated circuit and a semiconductor laser. Moreover, the processing method of the present invention can be applied to a subject having a mirror surface and can reflect X-rays. For example, the method can be applied to a substrate used for manufacturing a flat panel display.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A surface processing method for a subject which is subjected to the total-reflection X-ray fluorescence analysis, comprising the steps of:
   preparing a subject;
   dissolving at least contaminant lying on the measurement surface of the subject and entrapping the contaminant into a multitude of droplets without changing the in-plane distribution of the contaminant; and
   drying said multitude of droplets in place to obtain particle-shaped residues of the contaminant.

2. A surface processing method for a subject which is subjected to the total-reflection X-ray fluorescence analysis according to claim 1, wherein said multitude of droplets are obtained by dissolving the surface area of the subject and the contaminant lying inside the surface area of the subject.

3. A surface processing method for a subject which is subjected to the total-reflection X-ray fluorescence analysis according to claim 1, wherein said multitude of droplets are obtained by dissolving a film, contaminant lying on the film, and contaminant lying inside the film when the film is formed on the measurement surface of the subject.

4. A surface processing method for a subject which is subjected to the total-reflection X-ray fluorescence analysis according to claim 3, wherein said multitude of droplets are obtained by dissolving the surface area of the subject and the contaminant lying inside the surface area of the subject.

5. A surface processing method for a subject which is subjected to the total-reflection X-ray fluorescence analysis according to claim 1, wherein said step of dissolving at least the contaminant is effected while the subject is being heated.

6. A surface processing method for a subject which is subjected to the total-reflection X-ray fluorescence analysis according to claim 1, wherein said step of dissolving at least the contaminant is effected while the amount of material which takes a liquid form at normal temperatures is controlled.

7. A surface processing method for a subject which is subjected to the total-reflection X-ray fluorescence analysis according to claim 6, wherein height of a residual contaminant remaining on the measurement surface after said multitude of droplets are dried is not less than 0.1 μm and not more than 3 μm by controlling the amount of material which takes a liquid form at normal temperatures.

8. A surface processing method for a subject which is subjected to the total-reflection X-ray fluorescence analysis according to claim 1, wherein hydrofluoric acid, nitric acid, hydrochloric acid, sulfuric acid, hydrogen peroxide, ozone or a mixture of the above materials adequately mixed is used to dissolve at least the contaminant.

9. A surface processing method for a subject which is subjected to the total-reflection X-ray fluorescence analysis according to claim 1, wherein the subject has a mirror surface.

10. A surface processing method for a subject which is subjected to the total-reflection X-ray fluorescence analysis according to claim 1, wherein the subject is one of a semiconductor wafer, and a substrate used for manufacturing a flat panel display.

11. A surface processing method for a subject which is subjected to the total-reflection X-ray fluorescence analysis according to claim 10, wherein the semiconductor wafer is hydrophobic semiconductor wafer.

12. A surface processing method for a subject which is subjected to the total-reflection X-ray fluorescence analysis according to claim 1, wherein said multitude of droplets are obtained from a solvent for the contaminant.

13. A surface processing method for a subject which is subjected to the total-reflection X-ray fluorescence analysis according to claim 12, wherein the solvent is sprayed onto the measurement surface to obtain said multitude of droplets.

14. A surface processing method for a subject which is subjected to the total-reflection X-ray fluorescence analysis according to claim 12, wherein a dew of the solvent is formed on the measurement surface to obtain said multitude of droplets.

15. A surface processing method for a subject which is subjected to the total-reflection X-ray fluorescence analysis according to claim 12, wherein at least a contaminant lying on a film is dissolved into the multitude of droplets formed of the solvent when the film is formed on the measurement surface of the subject.

16. A surface processing method for a subject which is subjected to the total-reflection X-ray fluorescence analysis according to claim 15, wherein contaminants lying on and inside the film are dissolved into said multitude of droplets formed of the solvent.

17. A surface processing method for a subject which is subjected to the total-reflection X-ray fluorescence analysis according to claim 12, wherein said step of dissolving at least the contaminant is effected while heating the subject.

18. A surface processing method for a subject which is subjected to the total-reflection X-ray fluorescence analysis according to claim 12, wherein said step of dissolving at least the contaminant is effected while the amount of material which takes a liquid form at normal temperatures is controlled.

19. A surface processing method for a subject which is subjected to the total-reflection X-ray fluorescence analysis according to claim 18, wherein height of a residual contaminant remaining on the measurement surface after said multitude of droplets are dried is not less than 0.1 μm and not more than 3 μm by controlling the amount of material which takes a liquid form at normal temperatures.

20. A surface processing method for a subject which is subjected to the total-reflection X-ray fluorescence analysis according to claim 12, wherein hydrofluoric acid, nitric acid, hydrochloric acid, sulfuric acid, hydrogen peroxide, ozone or a mixture of the above materials adequately mixed is used to dissolve at least the contaminant.

21. A surface processing method for a subject which is subjected to the total-reflection X-ray fluorescence analysis according to claim 12, wherein the subject has a mirror surface.

22. A surface processing method for a subject which is subjected to the total-reflection X-ray fluorescence analysis according to claim 1, wherein the subject is one of a semiconductor wafer, and a substrate used for manufacturing a flat panel display.

* * * * *